US011412940B2

(12) United States Patent
Lin et al.

(10) Patent No.: US 11,412,940 B2
(45) Date of Patent: Aug. 16, 2022

(54) DYNAMIC MEASUREMENT DEVICE WITH A BLOOD PRESSURE DETERMINATION FUNCTION

(71) Applicants: Shiming Lin, Taipei (TW); BIV MEDICAL, LTD., Caotun Township, Nantou County (TW)

(72) Inventors: Shiming Lin, Taipei (TW); Shih-Wei Chiang, Taipei (TW); Cheng-Yan Guo, Taipei (TW); Tai-Cun Lin, Taipei (TW); Wei-Chih Huang, Taipei (TW); Chun-Nan Chen, Taipei (TW); Ya-Ting Chang, Taipei (TW)

(73) Assignees: Shiming Lin, Taipei (TW); BIV MEDICAL, LTD., Nantou County (TW)

( * ) Notice: Subject to any disclaimer, the term of this patent is extended or adjusted under 35 U.S.C. 154(b) by 593 days.

(21) Appl. No.: 16/465,379

(22) PCT Filed: Nov. 30, 2017

(86) PCT No.: PCT/CN2017/113924
§ 371 (c)(1),
(2) Date: May 30, 2019

(87) PCT Pub. No.: WO2018/099427
PCT Pub. Date: Jun. 7, 2018

(65) Prior Publication Data
US 2020/0000350 A1  Jan. 2, 2020

Related U.S. Application Data

(60) Provisional application No. 62/604,137, filed on Jun. 26, 2017, provisional application No. 62/498,991,
(Continued)

(51) Int. Cl.
*A61B 5/02* (2006.01)
*A61B 5/021* (2006.01)
(Continued)

(52) U.S. Cl.
CPC ........ *A61B 5/02108* (2013.01); *A61B 5/0006* (2013.01); *A61B 5/02116* (2013.01);
(Continued)

(58) Field of Classification Search
CPC ....... A61B 5/02; A61B 5/02125; A61B 5/282; A61B 5/02116; A61B 5/02444; A61B 5/6824
See application file for complete search history.

(56) References Cited

U.S. PATENT DOCUMENTS

2002/0001390 A1  1/2002  Kawaguchi
2003/0199776 A1  10/2003  Narimatsu et al.
(Continued)

FOREIGN PATENT DOCUMENTS

CN  104244814 A  12/2014
CN  104414627 A  3/2015
(Continued)

OTHER PUBLICATIONS

Chen et al.; "Continuous and Noninvasive Blood Pressure Measurement: A Novel Modeling Methodology of the Relationship Between Blood Pressure and Pulse Wave Velocity"; Jul. 1, 2009; Annals of Biomedical Engineering, vol. 37, pp. 1-12 (Year: 2009).*

*Primary Examiner* — Marjan Fardanesh
(74) *Attorney, Agent, or Firm* — Muncy, Geissler, Olds & Lowe, P.C.

(57) ABSTRACT

The present invention provides a dynamic measurement device with a blood pressure determination function, comprising: a heartbeat sensing module disposed on the chest area of a user wherein the heartbeat sensing module com-
(Continued)

prising a heart sound sensor for obtaining heartbeat signals; a pulse sensing module disposed on a limb area of the user, the pulse sensing module comprising a pulse wave sensor for obtaining pulse signals; and a data calculating module for calculating a mean arterial pressure and a value of systolic blood pressure and diastolic blood pressure based on the heartbeat signals and pulse signals. In addition to dynamically monitoring the blood pressure of a user for 24 hours, the present invention can dynamically monitor the heart sounds of the user for 24 hours individually in order to monitor user's physical condition. Therefore, the present invention has important medical meanings.

4 Claims, 8 Drawing Sheets

Related U.S. Application Data filed on Jan. 13, 2017, provisional application No. 62/497,740, filed on Dec. 1, 2016, provisional application No. 62/497,741, filed on Dec. 1, 2016.

(51) Int. Cl.
| | | |
|---|---|---|
| *A61B 5/00* | (2006.01) | |
| *A61B 5/024* | (2006.01) | |
| *A61B 5/022* | (2006.01) | |
| *A61B 7/04* | (2006.01) | |
| *A61B 5/30* | (2021.01) | |
| *A61B 5/282* | (2021.01) | |
| *A61B 5/332* | (2021.01) | |
| *A61B 5/25* | (2021.01) | |

(52) U.S. Cl.
CPC ...... *A61B 5/02225* (2013.01); *A61B 5/02438* (2013.01); *A61B 5/02444* (2013.01); *A61B 5/282* (2021.01); *A61B 5/30* (2021.01); *A61B 5/332* (2021.01); *A61B 5/681* (2013.01); *A61B 5/6823* (2013.01); *A61B 5/6824* (2013.01); *A61B 5/6841* (2013.01); *A61B 7/04* (2013.01); *A61B 5/02416* (2013.01); *A61B 5/25* (2021.01); *A61B 2562/0204* (2013.01); *A61B 2562/0209* (2013.01); *A61B 2562/0247* (2013.01)

(56) References Cited

U.S. PATENT DOCUMENTS

| | | | | |
|---|---|---|---|---|
| 2010/0160797 | A1* | 6/2010 | Banet | A61B 5/721 600/485 |
| 2011/0066009 | A1* | 3/2011 | Moon | A61B 5/0205 600/301 |

FOREIGN PATENT DOCUMENTS

| | | | |
|---|---|---|---|
| CN | 104873186 A | 9/2015 | |
| WO | WO-2016026698 A1 | 2/2016 | |
| WO | WO-2016040263 A1 * | 3/2016 | A61B 5/6824 |

* cited by examiner

Commercially available device

Commercially available device

Commercially available device

Commercially available device

Commercially available device

Commercially available device

DYNAMIC MEASUREMENT DEVICE WITH A BLOOD PRESSURE DETERMINATION FUNCTION

BACKGROUND OF THE INVENTION

1. Technical Field

The present invention relates to a dynamic measurement device, in particular a dynamic measurement device with a blood pressure determination function to dynamically measure blood pressure of a user.

2. Description of Related Art

Blood pressure is a crucial index for many cardiovascular diseases in the medical field, especially for a patient with hypertension. Being more aware of own blood pressure condition can effectively prevent complications that are fatal or affect other organs in the long term, such as intracerebral hemorrhage or other cerebrovascular diseases, myocardial infarction, heart failure, coronary artery disease, or other diseases associated with the heart, etc., even kidney disease or retinopathy, etc. As for healthy people, knowing own blood pressure condition can understand more about effects that some occasional events may cause to the blood pressure, such as emotions, diets, or smoking, etc., not to mention that patients with family history may have a chance of early diagnosis of whether they are having hypertension or borderline hypertension by taking good care of preventing their bodies from risk factors. In general, a sphygmomanometer mainly measures the pressure of the brachial artery utilizing an inflatable cuff, reflecting the turbulence of the blood flow to the pressure variation (a pulse wave) of the cuff during the pressure change in the inflation and the releasing of the cuff so as to determine the amplitude of the pressure in the cuff, thus blood pressure.

In addition to complications related to hypertension, valvular heart disease is another common and fatal cardiovascular disease, such as mitral stenosis and regurgitation, tricuspid stenosis and regurgitation, the aorta stenosis and regurgitation, pulmonary valve disease, etc. Blood flow in the human body is directed based mainly on cardiac muscle contraction and relaxation and the opening and closing of the heart valves, which are the key to keep blood flow moving in the right direction, and may cause blood flow to move abnormally if stenosis and regurgitation. For example, blood may be blocked if a valve opening is narrower than normal, and may be leaked through a gap if a valve is unable to be fully closed, thereby causing an extra burden to the heart. In the long term, said heart valve abnormalities may result in cardiomegaly, ventricular hypertrophy, and even heart failure. Clinically, auscultation is a way to hear noises generated from the aortic valve area so as to conduct diagnosis.

BRIEF SUMMARY OF THE INVENTION

The conventional sphygmomanometer is limited to location and time, and thus unable to facilitate real time measurement due to its lengthy steps of winding an inflatable cuff around the upper arm, obtaining pulse wave signals during the pressure releasing of the inflated cuff, and transmitting the signals to a processor via a path to calculate blood pressure accordingly. Furthermore, the way the conventional sphygmomanometer uses to exert pressure on a blood vessel and cut the blood flow may cause a patient having palpitations uncomfortable, and put the patient at risk. In addition, there is no device present that measures blood pressure and heart sounds simultaneously. Therefore, it is desirable to have a dynamic measurement device for blood pressure that tracks blood pressure, heart sounds, heart valve murmurs, and other physiological signals of a user in real time so as to improve personal health management, patients' quality of life, and reduce the medical burden imposed on individuals and society as a whole.

In view of the above mentioned, the primary objective of the present invention is to provide a dynamic measurement device with a blood pressure determination function, comprising: a heartbeat sensing module configured to be disposed on a chest area of a user, the heartbeat sensing module comprising a heart sound sensor for obtaining heartbeat signals; a pulse sensing module configured to be disposed on a limb area of the user, the pulse sensing module comprising a pulse wave sensor for obtaining pulse signals; and a data calculating module for calculating a mean arterial pressure (MAP) and a value of systolic blood pressure and diastolic blood pressure based on the heartbeat signals and pulse signals.

Further, the mean arterial pressure is calculated based on the formula (I) as follow:

$$\text{mean arterial pressure } (MAP) = a \times \left( \frac{L_P}{T_{PA}} \times c \right) + b \quad \text{formula (I)}$$

where $L_P$ is a length of an artery path through which a pulse wave propagates; $T_{PA}$ is a pulse arrival time (PAT); and a, b, and c each represents a correction parameter independently.

Further, the correction parameter a ranges from 0.01 to 0.15; the correction parameter b ranges from 0.01 to 0.15; and the correction parameter c ranges from 1 to 1000.

Further, the mean arterial pressure is calculated based on the formula (II) as follow:

$$\text{mean arterial pressure } (MAP) = A \left( \frac{L_P}{T_{PA}} \times C \right)^2 + B \quad \text{formula (II)}$$

where $L_P$ is a length of an artery path through which a pulse wave propagates; $T_{PA}$ is a pulse arrival time (PAT); and A, B, and C each represents a correction parameter independently.

Further, the correction parameter A ranges from 0.01 to 0.15; the correction parameter B ranges from 0.1 to 1.0; and the correction parameter C ranges from 1 to 1000.

Further, the heart sound sensor is configured to be disposed on the chest area of a user at a location corresponding to an aortic orifice, pulmonary orifice, tricuspid valve, or bicuspid valve.

Further, the heart sound sensor is an acoustic wave sensor.

Further, the pulse wave sensor is a/an Doppler radar, piezoelectric pressure sensor, piezoresistive pressure sensor, capacitive pressure sensor, acoustic wave sensor, ultrasonic sensor, or photoplethysmography (PPG) sensor.

Further, the pulse wave sensor is configured to be disposed on a wrist area at a location corresponding to a radial artery; and the length of an artery path through which the pulse wave propagates is the path length from the chest area to a wrist area.

Further, the pulse wave sensor is configured to be disposed on a wrist area at a location corresponding to a radial artery; and the length of an artery path through which the pulse wave propagates is the path length from the chest area to a wrist area.

Further, the heartbeat sensing module, the pulse sensing module, and the data calculating module are communicated by wired or wireless communication.

The dynamic measurement device with a blood pressure determination function of the present invention includes two separate sensing modules (i.e., the heartbeat sensing module and the pulse sensing module) that monitor the heartbeat and pulse of a user at the same time, and further includes the data calculating module that determines the blood pressure of the user by the afore obtained data, wherein the two sensing modules and the data calculating module can be communicated wirelessly. The present invention improves the lengthy way of exerting pressure on an artery in the upper arm with an inflatable cuff to cut the blood flow and measuring the blood pressure by transmitting pulse wave signals via a path, and eliminates the need to operate a bulky conventional diagnostic instrument by a skilled medical technician, so blood pressure measurement is not limited to location and time and can be monitored in real time. Moreover, in addition to dynamically monitoring the blood pressure of a user 24-hours, the present invention can dynamically monitor the heart sounds of the user 24-hours individually in order to check the abnormal heart sounds, such as the atrioventricular valve or the aortic orifice regurgitation, in order to realize the damages risk factors and occasional events may cause to the body.

DETAILED DESCRIPTION OF THE INVENTION

The details and technical solution of the present invention are hereunder described with reference to accompanying drawings. For illustrative sake, the accompanying drawings are not drawn to scale. The accompanying drawings and the scale thereof are not restrictive of the present invention.

The use of "comprise" means not excluding the presence or addition of one or more other components, steps, operations, or elements to the described components, steps, operations, or elements, respectively. Similarly, "comprise," "comprises," "comprising" "include," "includes," and "including" are interchangeable and not intended to be limiting. All ranges and values disclosed herein are inclusive and combinable. For examples, any value or point described herein that falls within a range described herein can serve as a minimum or maximum value to derive a sub-range, etc. As used herein and in the appended claims, the singular forms "a," "an," and "the" include plural referents unless the context dictates otherwise. The terms "a", "an," "the," "one or more," and "at least one," for example, can be used interchangeably herein.

Figure 1:
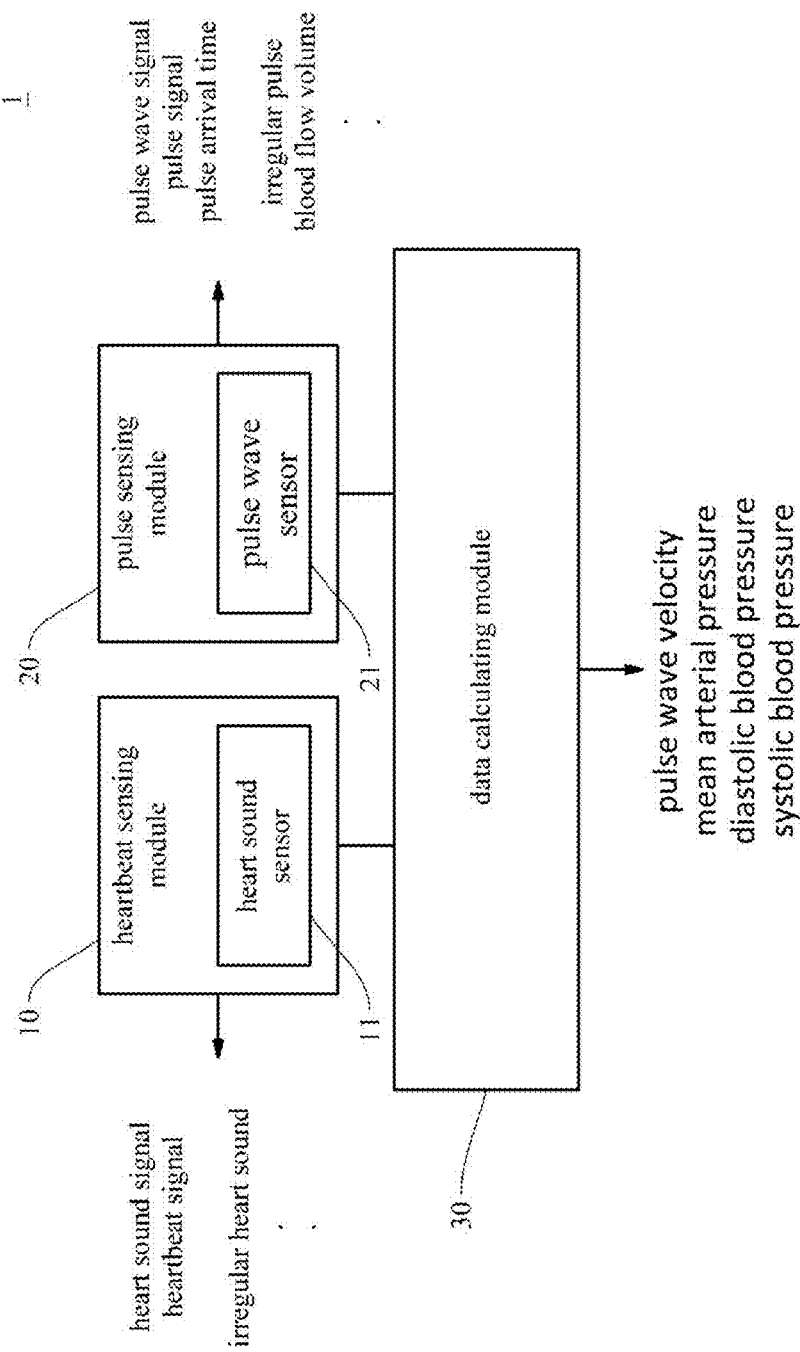
FIG. 1 is a block diagram of the dynamic measurement device according to a preferred embodiment of the present invention.

Referring to FIG. 1, the main purpose of the present invention is to provide a dynamic measurement device 1 with a blood pressure determination function, including a heartbeat sensing module 10 disposed on the chest area of a user that obtains heartbeat signals by a heart sound sensor 11, a pulse sensing module 20 disposed on a limb area of the user that obtains pulse signals by a pulse wave sensor 21, and a data calculating module 30 that calculates Mean Arterial Pressure (MAP) and systolic and diastolic blood pressures from the heartbeat signals and pulse signals.

The "heartbeat sensing module 10" described herein refers to a combination of the components having the ability to obtain heartbeat signals for a long period of time that may include hardware or software, or further combine an auxiliary. The hardware includes, but not limited to, a sensor including heartbeat measuring function, memory for receiving and saving data, and a processor for data processing and other related units. Said related units include, but not limited to, a signal amplifier, power supply, microcontroller unit, communication unit, power transfer unit, display unit 40, etc. Said software includes, but not limited to, data collection or feature extraction software, signal amplification software, and data analysis software, etc. Said auxiliary include, but not limited to, a patch, an electronic patch, and hand-held auxiliary, etc. In a preferred embodiment, the heartbeat sensing module is a heart sound sensor 11. In another preferred embodiment, the heart sound sensor 11 is a sound/acoustic wave sensor that obtains sound wave signals (or heart sound signals) from the heartbeat by the sound wave sensor, wherein the heart sound signals may be transferred into heartbeat data. In another preferred embodiment, the heartbeat sensing module 10 communicates with the pulse sensing module 20 and data calculating module 30. However, in other embodiments, the heartbeat sensing module 10 may work individually, which is not limited by the present invention. Said heartbeat sensing module 10 may work to obtain the heart sound signals of a user individually, since the heart sounds reflect how the heart valves operate, which reflects the states of the heart valves, myocardial function, and blood flow inside the heart based on the frequency, intensity, and relationships of the heart sounds to further determine whether an irregular heart sound or other heart-related abnormality occurs.

The "heart sounds" described herein generally refer to, in the medical field, noises generated during the cardiac cycle during which the heart valves open and close. For example, the first heart sound (S1) is generated by the closure of mitral and tricuspid valves when systole begins, and the second heart sound (S2) is generated by the closure of the arterial valves (including the aortic and pulmonic valves) when diastole begins. Therefore, the heart sound signals can be used to realize how the heart beats, and be transferred into the heartbeat signals. In a preferred embodiment, the heart sound sensor 11 is disposed on the chest area of a user where the aortic orifice, the pulmonary orifice, the mitral valve (or bicuspid valve), or the tricuspid valve are located. The heart sound sensor is attached to the aortic valve area to obtain the noises/abnormal sounds therefrom, which facilitates auscultation of heart-related diseases including, but not limited to, valvular heart diseases such as mitral stenosis and regurgitation, tricuspid stenosis and regurgitation, the aorta stenosis and regurgitation, pulmonary valve disease, etc.

The "pulse sensing module 20" described herein refers to a component combination having the ability to obtain pulse signals for a long period of time that may include hardware or software, or further combine an auxiliary. The hardware includes, but not limited to, a sensor including pulse measuring function, memory for receiving and saving data, and processor for data processing and other related units. Said related units include, but not limited to, a signal amplifier, power supply, microcontroller unit, communication unit, power transfer unit, display unit 40, etc. Said software includes, but not limited to, data collection or feature extraction software, signal amplification software, and data analysis software, etc. Said auxiliary include, but not limited to, a patch, an electronic patch, and hand-held auxiliary, etc. In a preferred embodiment, the pulse sensing module is a pulse wave sensor 21. In a preferred embodiment, the pulse wave sensor 21 is a/an Doppler radar, piezoelectric pressure sensor, piezoresistive pressure sensor, capacitive pressure sensor, acoustic wave sensor, ultrasonic sensor, or photoplethysmography (PPG), which is not limited by the present invention. Said pulse wave sensor 21 transfers the received pulse wave signals into pulse information. In another preferred embodiment, the pulse sensing module 20 communicates with the heartbeat sensing module 10 and data calculating module 30. However, in other embodiments, the pulse sensing module 20 may work individually, which is not limited by the present invention. An example of the independent working mode of said pulse sensing module 20 is to obtain pulse wave signals of a user to further determine whether an irregular pulse/heartbeat occurs. In addition to obtaining pulse wave or pulse, the pulse sensing module 20 of the present invention, according to different types of pulse sensors 21, may detect different elements: (for example) the sound of blood flow is detected using the acoustic wave sensor; the velocity of blood flow/pulse wave using the Doppler radar. The advantage of using the Doppler radar is that the sensor can be used in remote monitoring (i.e., the sensor is not in contact with the user), and can be attached to the limbs such as an arm to detect variation in pulse wave.

The "pulse wave" described herein refers to a curve of the pulse that records how the pressure applied to an artery changes when blood flow through the artery during the cardiac cycle. The curve is used to realize how the pulse changes, thereby determining if a lesion occurs and the corresponding symptoms. In a preferred embodiment, the pulse wave sensor 21 is used to detect arterial pulse, so the pulse wave sensor 21 is disposed on any location where the arterial pulse can be detected. In another preferred embodiment, the pulse wave sensor 21 is used to detect the pulse of the radial artery, so the pulse wave sensor 21 is disposed on any location of the limbs where the pulse of the radial artery can be detected. In a more preferred embodiment, the pulse wave sensor 21 is used to detect the pulse of the radial artery in a wrist, so the pulse wave sensor 21 is disposed on the wrist area where the location is corresponding to radial artery.

The "data calculating module 30" described herein refers to a combination of the components having the ability to process and compute signals that may include hardware or software, or further combine an auxiliary. The hardware includes, but not limited to memory for receiving and saving data, and a processor for data processing and other related units. Said related units include, but not limited to, a signal amplifier, power supply, microcontroller unit, communication unit, power transfer unit, display unit 40, etc. Said software includes, but not limited to, data collection or feature extraction software, signal amplification software, and data analysis software, etc. The data calculating module 30 calculates blood pressure based on the heartbeat signals captured by the heartbeat sensing module 10, the pulse signals captured by the pulse sensing module 20, and other parameters. In a preferred embodiment, the MAP is derived from the time difference between a heartbeat and a pulse, and is used to calculate the systolic and diastolic blood pressures of a user.

Blood pressure of the present invention is determined based on the relationship between pressure and pulse wave velocity (PWV). Each left ventricular contraction forms a plus wave that propagates through an artery and reaches peripheral arteries during a cardiac cycle. The PWV depends on arterial stiffness. The relation is described by equation (a) from Bramwell and Hill (1922):

$$PWV = \sqrt{\left(\frac{V}{\rho}\right)\left(\frac{dP}{dV}\right)}, \quad \text{equation (a)}$$

where $\rho$ is the density of blood. The arterial stiffness results from the transmural pressure applied to the artery wall. The pressure is associated with vascular geometry and the viscoelasticity of the artery wall. In general, the transmural pressure equals to the blood pressure of the artery, since the external pressure applied to the wall is negligible. Therefore, the arterial stiffness and the PWV are a function of the blood pressure of the artery. The relationship between the PWV and the blood pressure of the artery forms the basics of non-invasive blood pressure measurement. In addition, the PWV and diastolic blood pressure are most relevant to the MAP, which is described as follow:

$$PWV = fcn(MAP) \quad \text{equation (b).}$$

The relationship between the PWV and the MAP can be precisely described as a linear model. The relationship between the PWV and the MAP is described as follow:

$$PWV(t) = a \cdot MAP(t) + pwv_0 \quad \text{equation (c),}$$

where the slope a and a constant term $pwv_0$ vary from subject to subject. For measuring the PWV of a patient, a parameter, pulse arrival time ($T_{PA}$ or PAT), is monitored by the pulse sensing module in the present invention. By measuring, each PAT is the sum of two time intervals, vascular transit time (VTT) and pre-ejection period (PEP). The VTT is the time that the pulse wave propagates through the artery path. The PEP is the time interval between the electrical depolarization of the left ventricle and the beginning of ventricular ejection. The PEP includes electromechanical delay and isovolumic contraction of the left ventricle. The equation (d) is described for the PAT, which is as follow:

$$PAT = VTT + PEP = \left(\frac{L_t}{PWV}\right) + PEP, \quad \text{equation (d)}$$

where $L_t$ is the artery path through which the pulse propagates. Assume the PEP remains constant during the monitoring, the change in the PAT results in the change in the VTT directly. These two parameters are associated with the change in the MAP. To know the relationship between the PAT and the MAP, and the linear relationship between the MAP and the PWV $$PAT = \left(\frac{L_t}{PWV}\right) = \left(\frac{L_t}{aMAP + pwv_0}\right).\quad\text{equation (e)}$$

However, any error occurred from estimating the MAP based on the PAT may cause an inaccuracy in the unknown $pwv_0$, which can be corrected by time adjusting by tracking the changes in the PAT and the MAP. Furthermore, errors in the corrected MAP are less than the MAP before this correction, so the correction minimizes the errors of the estimated MAP associated with the a marked as an unknown slop. In summary, preferred formulas for calculating the MAP are thus derived by correcting the parameters of the above equations. The preferred formulas of the present invention minimize errors.

In a preferred embodiment, the MAP is calculated based on the formula (I) as follow:

$$\text{mean arterial pressure }(MAP) = a \times \left(\frac{L_P}{T_{PA}} \times c\right) + b,\quad\text{formula (I)}$$

where $L_P$ is the length of an artery path through which a pulse wave propagates, $T_{PA}$ is pulse arrival time (PAT), and a, b, and c each represents a correction parameter independently. Said correction parameters are preferred adjustments for the formula based on a database created from subjects. In a preferred embodiment, the correction parameter a ranges from 0.01 to 0.15, including, but not limited to, 0.01, 0.02, 0.03, 0.04, 0.05, 0.06, 0.07, 0.08, 0.09, 0.10, 0.11, 0.12, 0.13, 0.14, or 0.15; the correction parameter b ranges from 0.01 to 0.15, including, but not limited to, 0.01, 0.03, 0.05, 0.07, 0.09, 0.11, 0.13, or 015; and the correction parameter c ranges from 1 to 1000, including, but not limited to, 1, 10, 100, or 1000. In a more preferred embodiment, the correction parameter a ranges from 0.02-0.04; the correction parameter b ranges from 0.02-0.04; and the correction parameter c is 1. In a preferred embodiment, the pulse wave sensor 21 is used to detect the pulse of the radial artery in a wrist, so the length of an artery path through which a pulse wave propagates is the path length from the chest to a wrist. In the present invention, the PAT is the difference between the time by which a heartbeat signal is obtained by the heartbeat sensing module 10 and the time by which a pulse signal is obtained by the pulse sensing module 20. For example, the PAT is the difference between the time when the wave crest of an acoustic wave of a first heart sound (the beginning of systole) is obtained by the heart sound sensor 11 of the heartbeat sensing module 10 and the time when the wave crest of a pulse wave is obtained by the pulse wave sensor 21 (e.g., the Doppler radar) of the pulse sensing module 20 during a cardiac cycle; or the PAT can also be the difference between the time when the wave trough of an acoustic wave is obtained by the heart sound sensor 11 of the heartbeat sensing module 10 and the time when the wave trough of a pulse wave is obtained by the pulse wave sensor 21 (e.g., the Doppler radar) of the pulse sensing module 20 during a cardiac cycle. However, any corresponding point on the waves between the heartbeat and pulse signals may be used to obtain the PAT and the way of obtaining the PAT is not limited by the present invention.

In another preferred embodiment, the MAP is calculated based on the formula (II) as follow:

$$\text{mean arterial pressure }(MAP) = A\left(\frac{L_P}{T_{PA}} \times C\right)^2 + B,\quad\text{formula (II)}$$

where $L_P$ is the length of an artery path through which a pulse wave propagates, $T_{PA}$ is the PAT, and A, B, and C each represents a correction parameter independently. Said correction parameters are preferred adjustments for the formula based on a database created from subjects. In a preferred embodiment, the correction parameter A ranges from 0.01 to 0.15, including, but not limited to, 0.01, 0.02, 0.03, 0.04, 0.05, 0.06, 0.07, 0.08, 0.09, 0.10, 0.11, 0.12, 0.13, 0.14, or 0.15; the correction parameter B ranges from 0.1 to 1.0, including, but not limited to, 0.1, 0.2, 0.3, 0.4, 0.5, 0.6, 0.7, 0.8, 09, or 1.0; and the correction parameter C ranges from 1 to 1000, including, but not limited to, 1, 10, 100, or 1000. In a more preferred embodiment, the correction parameter A ranges from 0.02-0.10, the correction parameter B ranges from 0.1-1.0, and the correction parameter C is 100. In a preferred embodiment, the pulse wave sensor 21 is used to detect the pulse of the radial artery in a wrist, so the path length of an artery path through which a pulse wave propagates is the path length from the chest area to a wrist area. In the present invention, the PAT is the difference between the time by which a heartbeat signal is obtained by the heartbeat sensing module 10 and the time by which a pulse signal is obtained by the pulse sensing module 20. For example, the PAT is the difference between the time when the wave crest of an acoustic wave of a first heart sound (the beginning of systole) is obtained by the heart sound sensor 11 of the heartbeat sensing module 10 and the time when the wave crest of a pulse wave is obtained by the pulse wave sensor 21 (e.q., the Doppler radar) of the pulse sensing module 20 during a cardiac cycle; or the PAT can also be the difference between the time when the wave through of an acoustic wave is obtained by the heart sound sensor 11 of the heartbeat sensing module 10 and the time when the wave through of a pulse wave is obtained by the pulse wave sensor 21 (e.q., the Doppler radar) of the pulse sensing module 20 during a cardiac cycle. However, any corresponding point on the waves between the heartbeat and pulse signals may be used to obtain the PAT and the way of obtaining the PAT is not limited by the present invention.

The "communication" described herein refers to the communication among the components in the modules, the communication among the modules, or the communication between the modules and external devices. In particular, the communication among the modules refers to the communication among the heartbeat sensing module 10, the pulse sensing module 20, and the data calculating module 30. In a preferred embodiment, the heartbeat sensing module 10, the pulse sensing module 20, and the data calculating module 30 are communicated by wired or wireless communication. In a more preferred embodiment, the heartbeat sensing module 10, the pulse sensing module 20, and the data calculating module 30 are communicated by wireless communication. In particular, the wireless communication protocol may be one or more combination of Bluetooth, infrared communication (IR), Near Field Communication (NFC), Ultra-Wide Band (UWB), wireless local area network (WLAN), Wireless Gigabit Alliance (WiGig Alliance), Zigbee, Wireless USB, and Wi-Fi. The way of communication, communication protocol, or encryption are not limited by the present invention.

The present invention is more detailed illustrated by the example embodiments as below. While example embodiments are disclosed herein, it should be understood that they are used for illustrating the present invention, not for limiting the scope of the present invention.

Figure 2A:
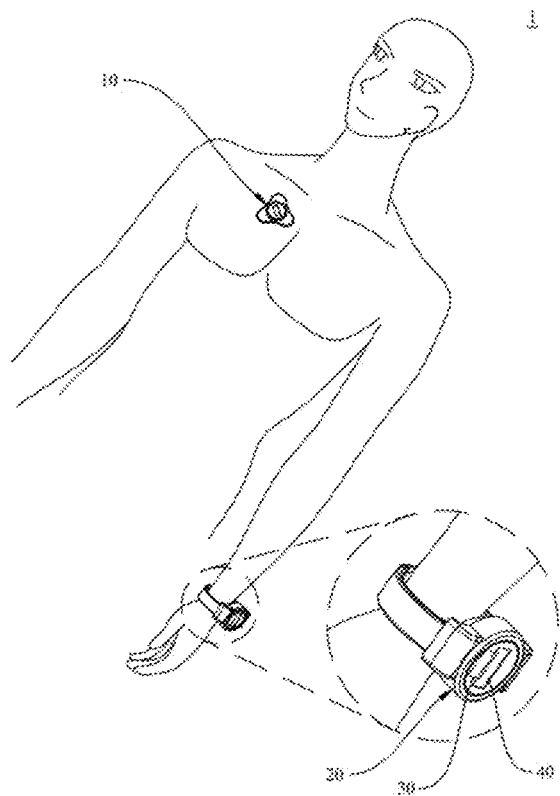
FIG. 2 (a) is a schematic diagram for illustrating the use state and (b) is an oscillogram of the dynamic measurement device according to Embodiment 1 of the present invention.
Figure 2B:
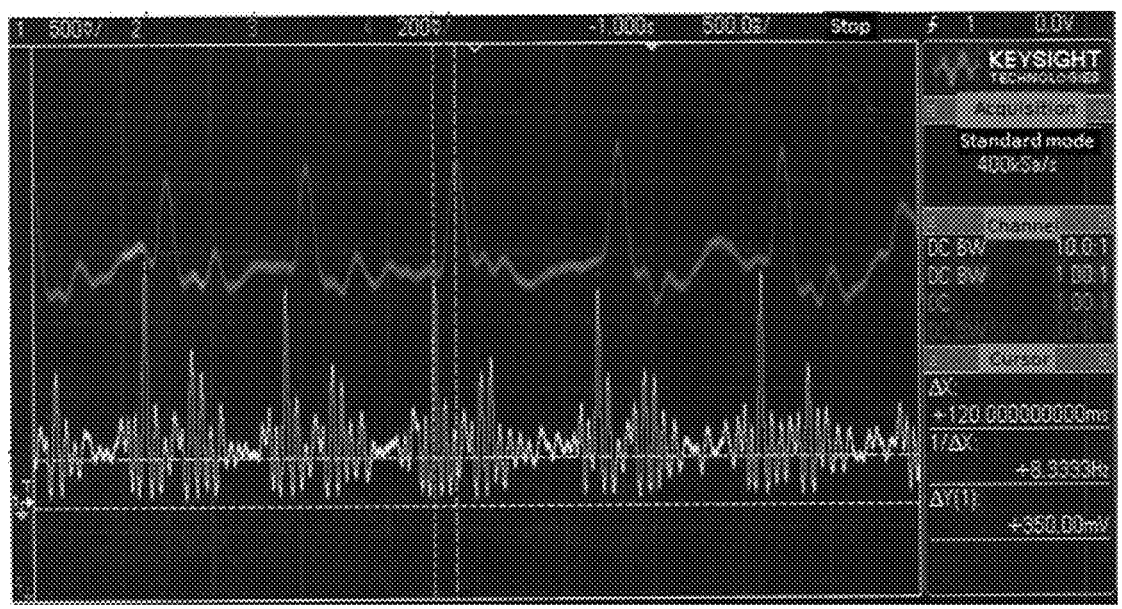

I. Embodiment 1—Time Between Aortic Orifice and Radial Artery Measurement Device Referring to FIGS. 2(a) and 2(b), FIG. 2 (a) is a schematic diagram for illustrating the use state and (b) is an oscillograms of the dynamic measurement device according to Embodiment 1 of the present invention.

In this embodiment, an acoustic wave sensor is used as the heart sound sensor 11 of the heartbeat sensing module 10 that is attached to the chest of a subject where the aortic valve area is located in order to obtain heart sound and heartbeat signals. In addition, the Doppler radar is used as the pulse wave sensor 21 of the pulse sensing module 20 that is attached to the wrist of the subject where the radial artery is located in order to obtain pulse wave and pulse signals. The obtained waves are shown in the FIG. 2(b) in which the waves below represents the heart sounds and heartbeat signals of the aortic orifice, and the waves represents the pulse wave and pulse signals of the radial artery. The left vertical dashed line indicates the time when the peak of the acoustic wave of a first heart sound (the beginning of systole) is obtained by the heart sound sensor 11 of the heartbeat sensing module 10 during a cardiac cycle, and the right vertical dashed line indicates the time when the peak of the pulse wave is obtained by the Doppler radar pulse wave sensor 21 of the pulse sensing module 20 during the same cardiac cycle. The difference (i.e., the time interval) between the two dashed lines is the PAT.

By the above disposition of the heartbeat sensing module 10 and the pulse sensing module 20, the PWV from the aortic valve to the radial artery can be calculated, and arterial pressures such as the MAP and the systolic and diastolic blood pressures can thus be calculated by the data calculating module 30. In addition, the heartbeat sensing module 10 of the present invention may be used individually to detect whether the subject has irregular heart sounds. Alternatively, the heartbeat sensing module 10 and pulse sensing module 20 can be used simultaneously to detect whether the subject has irregular PWV of the aorta.

[Example 1]—Heart Sound Correlation Test: Acoustic Wave Sensor vs. Commercially Available Electronic Stethoscope For the purpose of verifying the heart sound detection function of the heart sound sensor 11 of the present invention, 25 people including healthy and patients who were admitted with aortic stenosis were studied during simultaneous a commercially available electronic stethoscope and the heart sound sensor 11 in the Embodiment 1 recording. The correlation between the first heart sound (S1) and the second heart sound (S2) recorded by the commercial electronic stethoscope (3M Littmann 3200®) and by using the heart sound sensor 11 in the Embodiment 1 were measured.

Figure 4A:
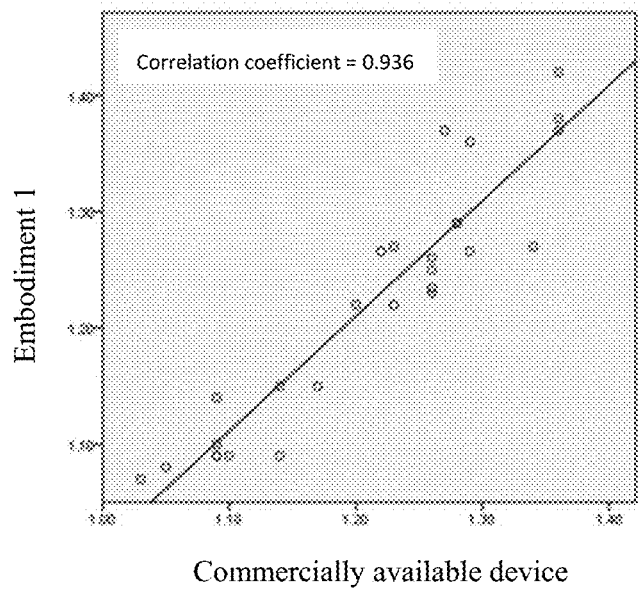
FIGS. 4 (a) and (b) are dispersion graphs according to the correlation test of Example 1 of the present invention.
Figure 4B:
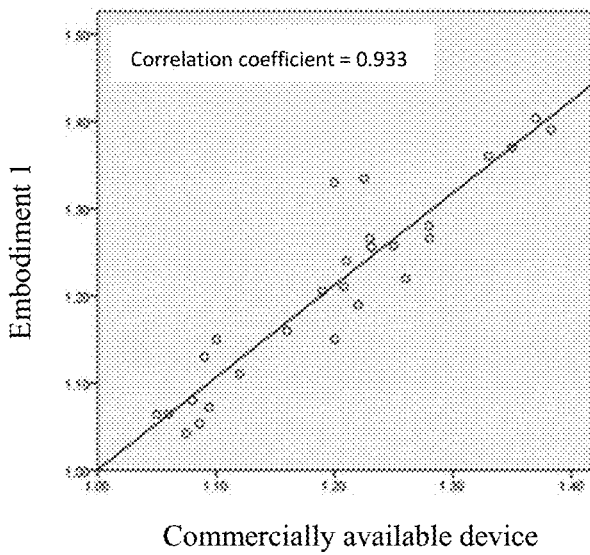

The results are shown in the FIGS. 4(a) and 4(b). During simultaneous the heart sound sensor 11 of the Embodiment 1 and the electronic stethoscope detection including 25 average values of first sound intervals, the first sound peak intervals obtained by the heart sound sensor 11 is significantly correlated with the first sound peak intervals obtained by the electronic stethoscope (correlation coefficient $R=0.936$, $p<0.001$). The dispersion graph of FIG. 4(b) showed a linear trend line. Furthermore, as shown in the FIG. 4(b), it is also found that the second sound peak (S2) intervals of the heart sound sensor 11 of the Embodiment 1 is significantly correlated with the second sound peak (S2) intervals of the electronic stethoscope (correlation coefficient $R=0.933$, $p<0.001$).

Accordingly, the heart sound sensor 11 of the present invention is able to measure the heart sound signals, including the first and second heart sounds during the cardiac cycle, accurately. Therefore, these heart sound signals can be used to obtain information related to the heartbeat, and can be further used to detect if any irregular heart sound.

[Example 2]—the PWV of the Aorta Correlation Test: Embodiment 1 vs. Commercially Available Sphygmomanometer In order to understand whether the measurement results, especially in the aortic pulse wave velocity, of the present invention differs from the measurement results of a commercially available arm brachial artery blood pressure, the Embodiment 1 and a commercially available arm brachial artery pressure (BAP) monitor (HBP-9092 available from OMRON) are used to measure the aortic PWV from aortic valve area to the radial artery of 25 subjects including healthy and patients who were admitted with aortic stenosis. The results from the two devices are noted for correlation analysis.

Figure 5:
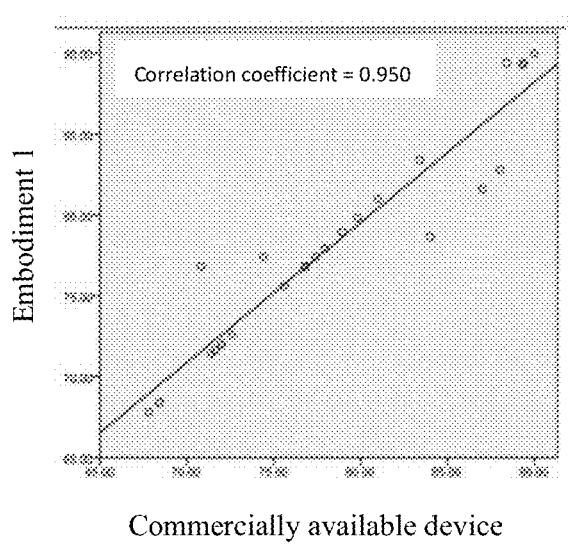
FIG. 5 is a dispersion graph according to the correlation test of Example 2 of the present invention.

As shown in the FIG. 5, The PWVs of the artery of the 25 subjects obtained from the Embodiment 1 and the commercially available arm brachial artery pressure monitor, respectively have a significant correlation (correlation coefficient $R=0.950$, $p<0.001$), which can be seen by a linear relationship in the figure.

In the present invention, the PWV can be accurately measured, be used to obtain information related to the pulse wave, and be further used to detect whether an irregular pulse or PWV occurs.

[Example 3]—the MAP Correlation Test: Embodiment 1 vs. Commercially Available Sphygmomanometer For the purpose of realizing whether the artery blood pressure obtained by the present invention differs from that obtained by a commercially available device, the Embodiment 1 and the commercially available arm brachial artery pressure monitor (HBP-9020 available from OMRON) are used to measure the MAP of 12 healthy subjects and 18 subjects who were admitted with hypertension. The results from the two devices are noted for correlation analysis.

Figure 6A:
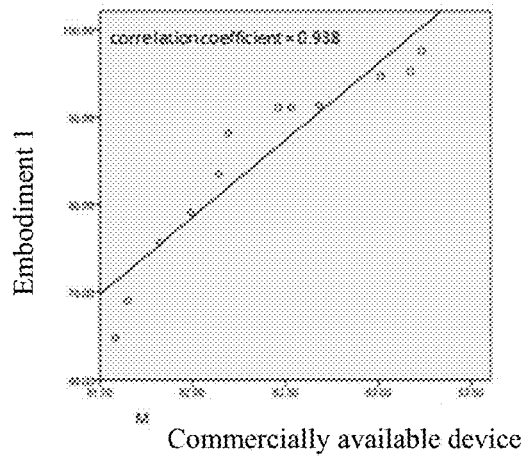
FIGS. 6 (a) and (b) are dispersion graphs according to the correlation test of Example 3 of the present invention.
Figure 6B:
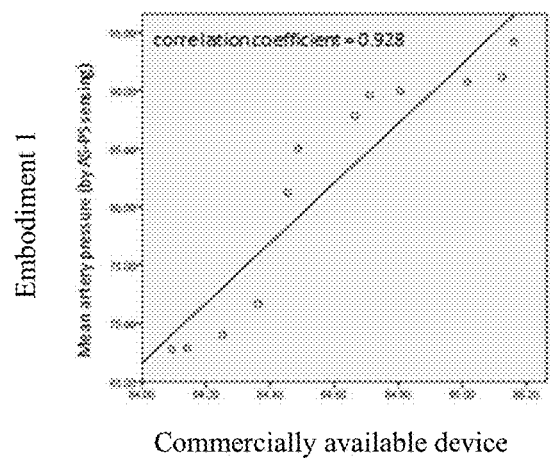
Figure 6C:
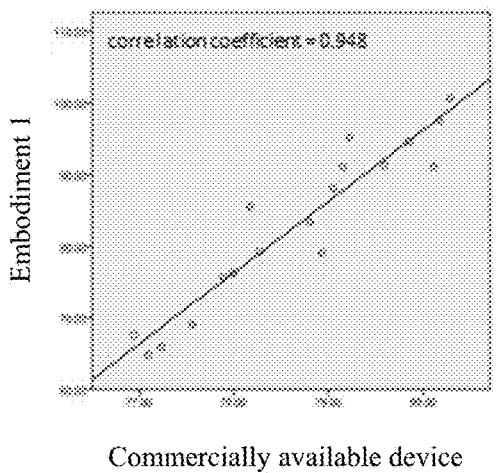
Figure 6D:
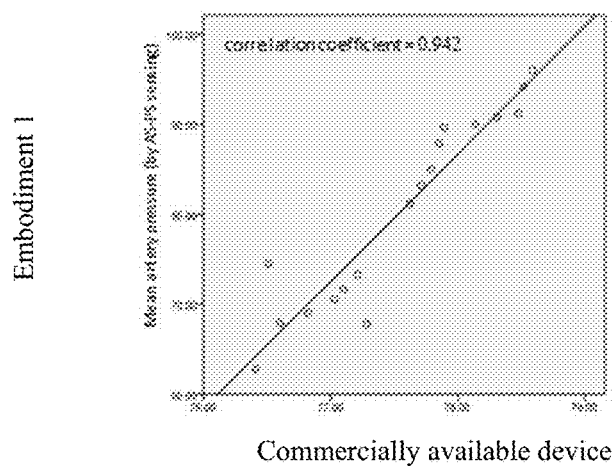

The results are shown in the FIGS. 6(a)-6(d) in which the FIG. 6(a) shows correlation analysis of the MAP results of the 12 healthy subjects using the commercially available sphygmomanometer first, and then the Embodiment 1(correlation coefficient $R=0.938$); the FIG. 6(b) shows correlation analysis of the MAP results of the 12 healthy subjects using the Embodiment 1 first, and then the commercially available sphygmomanometer (correlation coefficient $R=0.928$); the FIG. 6(c) shows correlation analysis of the MAP results of the 18 subjects with hypertension using the commercially available sphygmomanometer first, and then the Embodiment 1(correlation coefficient $R=0.948$); and the FIG. 6(d) shows correlation analysis of the MAP results of the 18 subjects with hypertension using the Embodiment 1 first, and then the commercially available sphygmomanometer (correlation coefficient R=0.942). It is noted that the resulting MAPs from the present invention and the commercially available sphygmomanometer have a significant correlation, regardless of the order of measurement of the two devices or whether the subjects suffer from hypertension.

Therefore, in the present invention, the MAP can be accurately measured, be calculated by the data calculating module 30, and further be used to detect the systolic and diastolic blood pressures of a subject, in which dynamic blood pressure measuring for multiple hours can thus be achieved and is not limited by location.

[Examples 4-14]—Correction Parameters Adjustment

For the purpose of obtaining better blood pressure, many commercially available sphygmomanometers with different brands or models are used to adjust correction parameters in the formulas (I) and (II) from the Embodiment 1. The resulting MAPs obtained from the different sphygmomanometers in multiple sets of experiments are used to adjust correction parameters. The resulting correction parameters are shown in the Table 1.

TABLE 1

| Formula (I) | | Correction Parameter a | Correction Parameter b | Correction Parameter c |
| --- | --- | --- | --- | --- |
| Example 4 | OMRON sphygmomanometer (Model: HBP) | 0.0376 | 0.0343 | 1 |
| Example 5 | OMRON sphygmomanometer (Model: HBP) | 0.0357 | 0.0348 | 1 |
| Example 6 | OMRON sphygmomanometer (Model: REM) | 0.0321 | 0.0340 | 1 |
| Example 7 | OMRON sphygmomanometer (Model: REM) | 0.0396 | 0.0402 | 1 |

| Formula (II) | | Correction Parameter A | Correction Parameter B | Correction Parameter C |
| --- | --- | --- | --- | --- |
| Example 8 | OMRON sphygmomanometer (Model: REM) | 0.0228 | 0.1098 | 1 |
| Example 9 | OMRON sphygmomanometer (Model: REM) | 0.0302 | 0.2558 | 1 |
| Example 10 | OMRON sphygmomanometer (Model: REM) | 0.0344 | 0.5548 | 1 |
| Example 11 | OMRON sphygmomanometer (Model: REM) | 0.0252 | 0.187 | 1 |
| Example 12 | OMRON sphygmomanometer (Model: REM) | 0.02692 | 0.8708 | 100 |
| Example 13 | OMRON sphygmomanometer (Model: HBP) | 0.0856 | 0.1030 | 100 |
| Example 14 | Terumo sphygmomanometer (Model: PS) | 0.022948 | 0.980498 | 100 |

Based on the above experiments, the preferred ranges of the correction parameters of formula (I) are 0.03-0.04 for the correction parameter a, 0.03-0.04 for the correction parameter b, and 1 for the correction parameter c, while the correction parameters of formula (II) are 0.02-0.04 for the correction parameter A, 0.1-1.0 for the correction parameter B, and 1 or 100 for the correction parameter C.

In addition, for the purpose of realizing the difference between the measurement results from the two formulas and a commercially available sphygmomanometer, the formulas (I) and (II) and the commercially available sphygmomanometer are used for correlation analysis.

[Example 15]—Correlation Test

Figure 7:
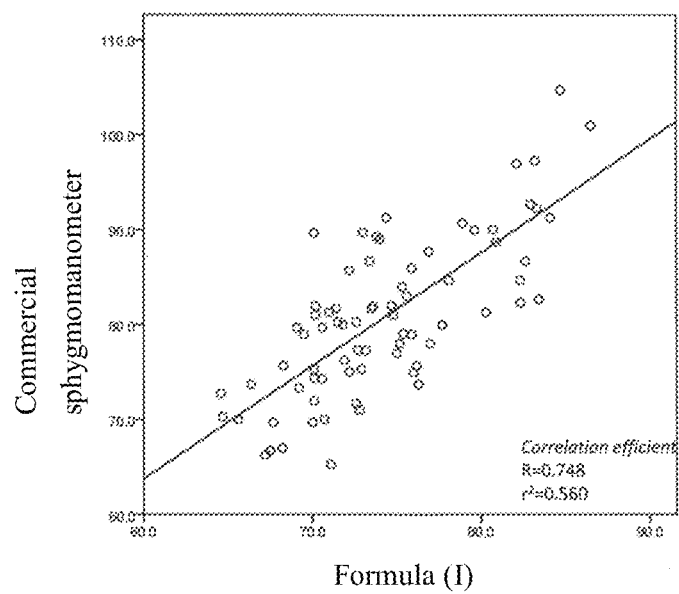
FIG. 7 is a dispersion graph according to the correlation test of formula (I) of Example 15 of the present invention.

In the FIG. 7, the correlation analysis for the MAPs obtained by the data calculating module of the present invention using the formula (I) and measured by the commercially available sphygmomanometer (HBP-9092 available from OMRON), respectively, is shown. In this example, the correction parameters used in the formula (I) are 0.037683883 for the correction parameter a, 0.033357854 for the correction parameter b, and 1 for the correction parameter c. It can be observed that there is a clear linear relationship between the two (correlation coefficient R=0.748).

Figure 8:
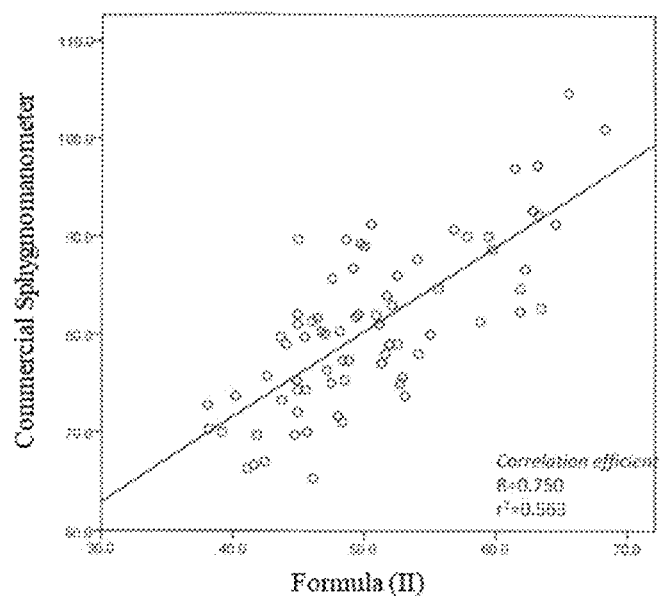
FIG. 8 is a dispersion graph according to the correlation test of formula (II) of Example 15 of the present invention.

In the FIG. 8, the correlation analysis for the MAPs obtained by the data calculating module of the present invention using the formula (II) and measured by the commercially available sphygmomanometer (HBP-9092 available from OMRON), respectively, is shown. In this example, the correction parameters used in the formula (II) are 0.085562426 for the correction parameter A, 0.102976872 for the correction parameter B, and 100 for the correction parameter C. Similarly, it can be observed that there is a clear linear relationship between the results from the present invention and the commercially available sphygmomanometer (correlation coefficient R=0.750).

II. Embodiment 2—Time Between Pulmonary Orifice and Radial Artery Measurement Device Referring to FIG. 3, FIG. 3 (a) is a schematic diagram for illustrating the use state and (b) is an oscillograms of the dynamic measurement device according to Embodiment 2 of the present invention.

Figure 3A:
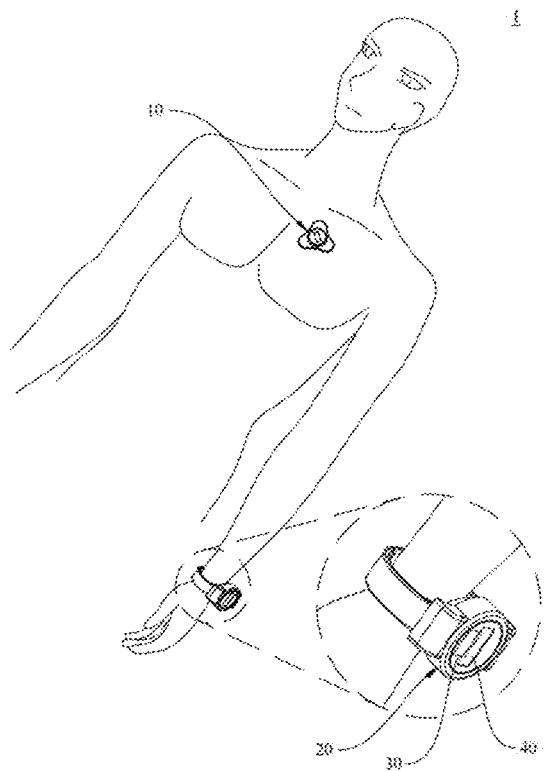
FIG. 3 (a) is a schematic diagram for illustrating the use state and (b) is an oscillogram of the dynamic measurement device according to Embodiment 2 of the present invention.
Figure 3B:
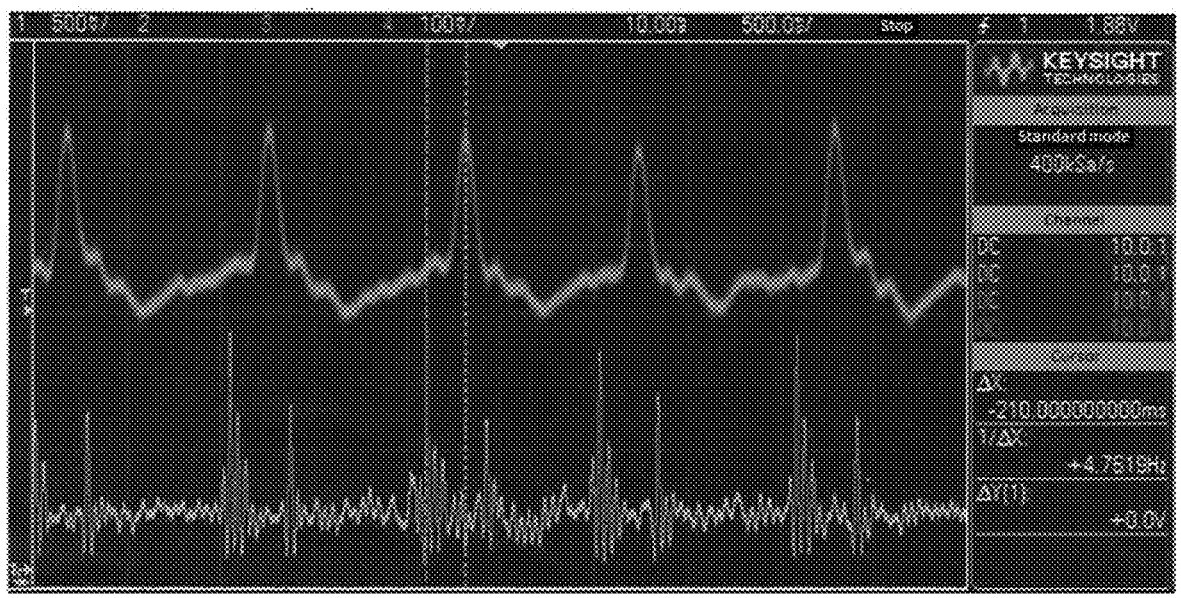

The difference between the Embodiment 2 and 1 is that the heartbeat sensing module 10 in the Embodiment 2 is attached to the chest where the pulmonary orifice is located as shown in the FIG. 3(a), and the rest of arrangement the Embodiment 2 is the same as the Embodiment 1. The obtained waves are shown in the FIG. 3(b) in which the waves below represents the heart sounds and heartbeat signals of the pulmonary orifice, and the waves above represents the pulse wave and pulse signals of the radial artery. The left vertical dashed line indicates the time when the peak of the acoustic wave of a first heart sound (the beginning of systole) is obtained by the heart sound sensor 11 of the heartbeat sensing module 10 during a cardiac cycle, and the right vertical dashed line indicates the time when the peak of the pulse wave is obtained by the Doppler radar pulse wave sensor 21 of the pulse sensing module 20 during the same cardiac cycle. The difference (i.e., the time interval) between the two dashed lines is the PAT.

By the above disposition of the heartbeat sensing module 10 and the pulse sensing module 20, the PWV from the pulmonary orifice to the radial artery can be calculated, and blood pressures such as the MAP of the radial artery and the systolic and diastolic blood pressures can thus be calculated by the data calculating module 30. In addition, the heartbeat sensing module 10 of the present invention may also be used individually to detect whether the subject has irregular heart sounds or noises. Alternatively, the heartbeat sensing module 10 and pulse sensing module 20 can be used simultaneously to detect whether the subject has irregular PWV of the aorta. In summary, the dynamic measurement device with a blood pressure determination function of the present invention includes two separate sensing modules (i.e., the heartbeat sensing module and the pulse sensing module) that monitor the heartbeat and pulse of a user at the same time, and further includes the data calculating module that determines the blood pressure of the user by the afore obtained data, wherein the two sensing modules and the data calculating module can be communicated wirelessly. The present invention improves the lengthy way of exerting pressure on an artery in the upper arm with an inflatable cuff to cut the blood flow and measuring the blood pressure by transmitting pulse wave signals via a path, so blood pressure measurement is not limited to location and time and can be monitored in real time. Moreover, in addition to dynamically monitoring the blood pressure of a user for 24 hours, the present invention can dynamically monitor the heart sounds of the user 24-hours individually in order to check the abnormal heart sounds, such as the atrioventricular valve or the aortic orifice regurgitation. The present invention allows for understanding of the damages occasional events such as emotions, diets, or smoking, etc. may cause to the body, and health management of patients with hypertension, which is crucial in preventive healthcare, and thus possesses extremely high industrial applicability.

The above is the detailed description of the present invention. However, the above is merely the preferred embodiment of the present invention and cannot be the limitation to the implement scope of the present invention, which means the variation and modification according to the present invention may still fall into the scope of the invention.

What is claimed is:

1. A dynamic measurement device with a blood pressure determination function, comprising:
    a heartbeat sensing module configured to be disposed on a chest area of a user, the heartbeat sensing module comprising a heart sound sensor for obtaining heartbeat signals;
    a pulse sensing module configured to be disposed on a limb area of the user, the pulse sensing module comprising a pulse wave sensor for obtaining pulse signals; and
    a data calculating module for calculating a mean arterial pressure (MAP) and a value of systolic blood pressure and diastolic blood pressure based on the heartbeat signals and pulse signals;
    wherein the mean arterial pressure is calculated based on the formula (I) or formula (II) as follow:

$$\text{mean arterial pressure } (MAP) = a \times \left(\frac{L_P}{T_{PA}} \times c\right) + b, \quad \text{formula (I)}$$

or $$\text{mean arterial pressure } (MAP) = A\left(\frac{L_P}{T_{PA}} \times C\right)^2 + B; \quad \text{formula (II)}$$

where $L_P$ is a length of an artery path through which a pulse wave propagates; $T_{PA}$ is a pulse arrival time (PAT); and a, A, b, B, c and C each represents a correction parameter independently;
    wherein the correction parameter a ranges from 0.01 to 0.15; the correction parameter b ranges from 0.01 to 0.15; the correction parameter c ranges from 1 to 1000; the correction parameter A ranges from 0.01 to 0.15; the correction parameter B ranges from 0.1 to 1.0; and the correction parameter C ranges from 1 to 1000;
    wherein the pulse wave sensor is configured to be disposed on a wrist area at a location corresponding to a radial artery; and the length of an artery path through which the pulse wave propagates is a path length from the chest area to a wrist area;
    wherein the heartbeat sensing module, the pulse sensing module, and the data calculating module are in communication with each other by wireless communication.

2. The dynamic measurement device of claim 1, wherein the heart sound sensor is configured to be disposed on the chest area of a user at a location corresponding to an aortic orifice, pulmonary orifice, tricuspid valve, or bicuspid valve.

3. The dynamic measurement device of claim 1, wherein the heart sound sensor is an acoustic wave sensor.

4. The dynamic measurement device of claim 1, wherein the pulse wave sensor is a/an Doppler radar, piezoelectric pressure sensor, piezoresistive pressure sensor, capacitive pressure sensor, acoustic wave sensor, ultrasonic sensor, or photoplethysmography (PPG) sensor.

* * * * *